United States Patent [19]

Gosthnian et al.

[11] Patent Number: 4,923,475

[45] Date of Patent: May 8, 1990

[54] INFLATABLE LIMB PROSTHESIS WITH PREFORMED INNER SURFACE

[76] Inventors: Barry M. Gosthnian, 5211 E. Trindle Rd., Apt. 3, Mechanicsburg, Pa. 17055; Hugh Herr, R.D. 1, Box 272, Holtwood, Pa. 17532

[21] Appl. No.: 312,448

[22] Filed: Feb. 21, 1989

[51] Int. Cl.⁵ .............................. A61F 2/80; A61F 2/78
[52] U.S. Cl. ......................................................... 623/37
[58] Field of Search .................................... 623/33–37, 623/27

[56] References Cited

U.S. PATENT DOCUMENTS

| | | | |
|---|---|---|---|
| 3,393,407 | 7/1968 | Kandel | 623/37 |
| 4,432,101 | 2/1984 | Johnson | 623/37 |

FOREIGN PATENT DOCUMENTS

| | | | |
|---|---|---|---|
| 507275 | 11/1954 | Canada | 623/37 |
| 2420335 | 10/1979 | France | 623/37 |
| 2586555 | 3/1987 | France | 623/33 |
| 7080 | 8/1898 | Norway | 623/37 |

Primary Examiner—Ronald L. Frinks
Attorney, Agent, or Firm—John G. Gilfillan, III

[57] ABSTRACT

A prosthesis having a stump-receiving socket and a plurality of inflatable bladders with a means for the user to vary the pressures therein. The inflatable bladders each include a relatively soft, flexible membrane made of a suitable material such as polyurethane. The membranes are shaped to meet the anatomical characteristic of the wearer. Those membranes located adjacent the weight-bearing portions of the stump will provide a relatively soft uniform surface to support the stump. For those locations near the weight-bearing portions of the stump that should not be subjected to pressures, the adjacent bladder areas are non-inflatable and, therefore, not force inducing. The static pressures in the various bladders are independent of each other and may be regulated by the user.

6 Claims, 2 Drawing Sheets

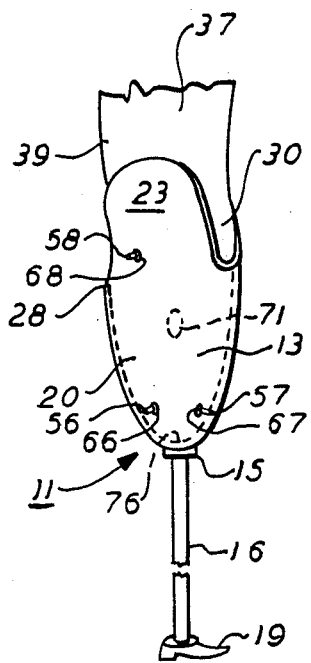
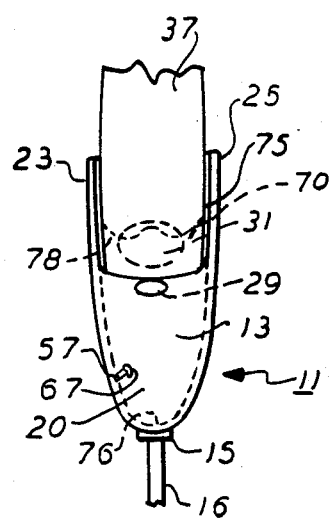
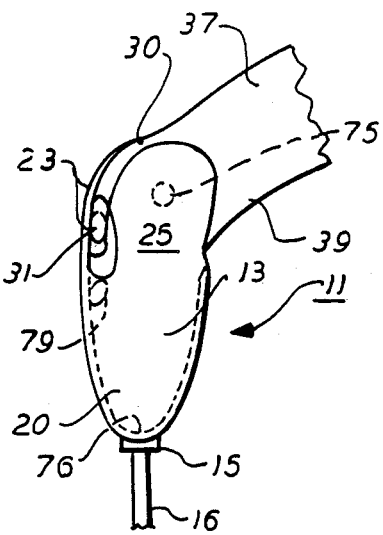
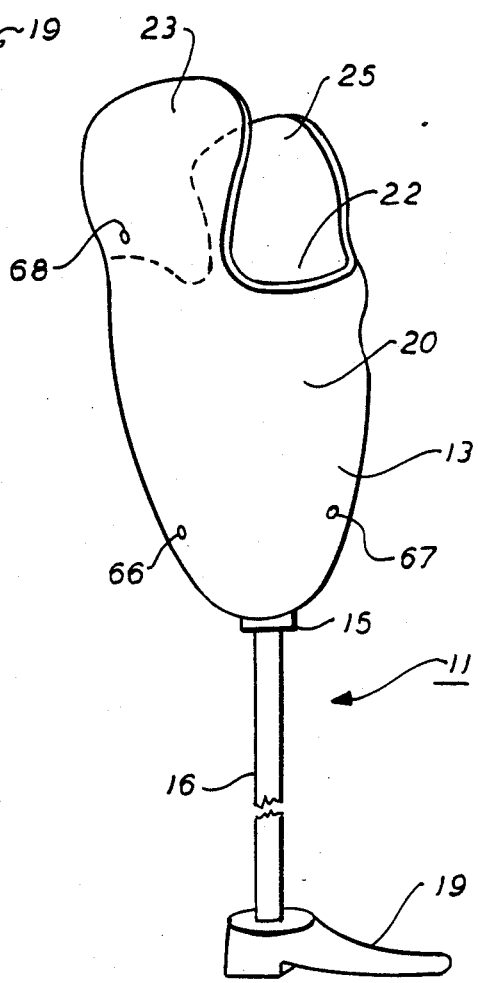

INFLATABLE LIMB PROSTHESIS WITH PREFORMED INNER SURFACE

BACKGROUND OF THE INVENTION

The present invention relates to prostheses and more particularly to artificial limbs having means for supporting the terminus or stump of an amputated body member.

Artificial limbs are usually provided with a socket into which the amputated end of a body member is inserted. Such stump-receiving sockets normally perform a number of critical functions. For example, one important socket function, especially if the limb is an artificial leg, is providing a weight-bearing surface for the stump. Another important socket function is supplying lateral support to the sump to maintain stability for the wearer. Other typical functions of a socket include attaching the artificial limb to the wearer and maintaining mechanical freedom of motion for a joint such as a knee, or the like.

One of the most critical problems confronting developers of such limbs has been the reduction of unwanted pressures on critical anatomical portions of the stump, such as bones, nerves, veins, arteries, ligaments, tendons, and the like. When the prosthesis is an artificial leg, the weight-bearing characteristics of the stump-supporting socket become a critical consideration. This is so because the required support and stability must be accomplished without causing undesirable pressures at those critical anatomical points on the stump, i.e., veins, ligaments, nerves, bones, etc. It is equally important, however, that there be a relatively uniform surface over the area of contact between the prosthesis and the stump. It has been found that significant abrasions of the skin often occur at those areas where movement and rubbing occurs between the skin and the supporting surfaces.

In the past, prosthesis devices have been proposed which include inflatable collars, bags, membranes, etc. that seat in or around the usual stump-receiving socket for the purpose of providing a cushioned support for the stump. Such devices have not been entirely satisfactory in that either the weight-bearing surface is unduly small, thereby creating large forces at the supporting surfaces, or the inflatable supports completely encircle the stump, thereby causing pressures and constricting forces at undesirable points, or there are unacceptable numbers of discontinuities in the support surface, thereby creating areas of potential skin abrasions. Additionally, it has also been typical for the collar, bag or membrane to have a single inflatable chamber thereby causing instabilities due to undamped motions when in dynamic use. These problems are overcome by the present invention.

SUMMARY OF THE INVENTION

The general purpose of this invention is to provide an inflatable stump-receiving socket for a prosthesis device capable of maximizing the weight-bearing area, thereby reducing the supporting force per unit area, while selectively minimizing or eliminating pressures on critical anatomical points and minimizing the areas of discontinuities in the supporting surfaces. To attain this, the present invention provides a stump-receiving socket having a plurality of inflatable bladders. The inflatable bladders each include a relatively soft, flexible membrane made of a suitable material such as polyurethane. The membranes are shaped to meet the anatomical characteristics of the wearer while the outer surfaces of the membranes have a suitable cooefficient of static friction to prevent movement and rubbing between the skin and the membrane to avoid abrasions. Those areas of the membranes located adjacent the weight-bearing portions of the stump provide a relatively soft uniform surface to support the stump. For those locations near the weight-bearing portions of the stump that should not be subjected to pressures, the adjacent bladder areas are non-inflatable and, therefore, not force inducing. The non-inflatable areas are also used to define the perimeters of the various bladders thereby minimizing the size of such areas. Further, undamped motions during use are reduced significantly by the provision of independent bladders. Additionally, one of the bladders provides stability as well as a means for holding the prosthesis on the stump. The static pressures in the various bladders are independent of each other and may be selectively regulated by the user to different pressures or to equal pressures through multiple valves or through common valves, respectively.

The exact nature of this invention as well as other objects and advantages thereof will be readily apparent from consideration of the following specification relating to the annexed drawing in which:

BRIEF DESCRIPTION OF THE DRAWINGS

FIG. 1 shows a side elevation view of the preferred embodiment on a leg with the knee unflexed:

FIG. 2 shows a front elevation view of the device shown in FIG. 1;

FIG. 3 shows a perspective view of the device shown in FIG. 1 with the knee flexed;

FIG. 4 shows a perspective view of a portion of the device shown in FIG. 1;

DETAIL DESCRIPTION OF THE INVENTION

Figure 6:
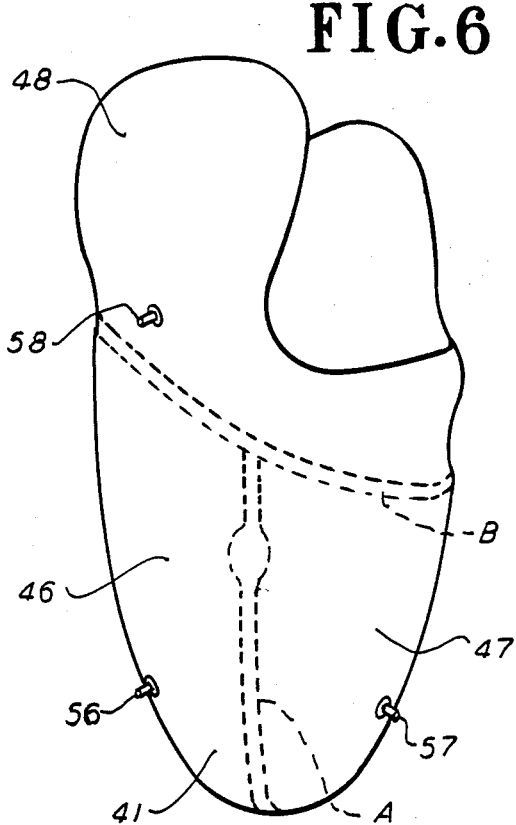
FIG. 6 shows a perspective view of the device shown in FIG. 5.

Referring now to the drawings there is shown an artificial leg 11 of the type to be worn by a below-the-knee amputee. In the present disclosure, the preferred embodiment is illustrated as a prosthetic appliance of the to be worn as an artificial leg by a below-the-knee amputee. It will be appreciated, however, that the inventive embodiment has equal application to other types of artificial limbs and like prosthetic appliances.

The leg 11 includes a rigid shell 13 fixed to the upper end 15 of a vertical brace 16. An artificial foot 19 is fixed to the lower end of brace 16. Brace 16 and foot 19 may be selected from the numerous devices already available to those skilled in these arts. It is preferable that the vertical brace 16, the foot 19 and the shell 13 be made of a strong, rigid, lightweight material such as carbon fiber.

The shape of the inside surface 22 of shell 13 may be molded to assume the general anatomical configuration of the limb to be supported. The size of the shell 13 should be slightly greater than the limb to provide sufficient clearance for a sock 40. The presently illustrated shell 13 is shown to have a generally cup-shaped lower section 20 with a pair of opposed ears 23, 25 extending upwardly therefrom. Ears 23, 25 are of a size to extend on opposite sides of a knee 30 to provide lateral support and stability to the knee 30 while permitting the knee cap 31 to project forwardly and the back 39 of the leg 37 to freely rotate rearwardly.

It is noted at this point that throughout the drawings, the leg 37 depicts the right leg. The invention, of course, is equally applicable to the left leg as well as other body members.

The shell 13 primarily supports the wearer's weight which is transferred from the femur to the tibia via the condylar and finally to a sock 40 mounted in socket 13. In addition to supporting the user's weight and providing lateral stability to the amputated limb, the socket 13 is also designed as a means to help retain the prosthesis on the amputated limb.

Figure 8:
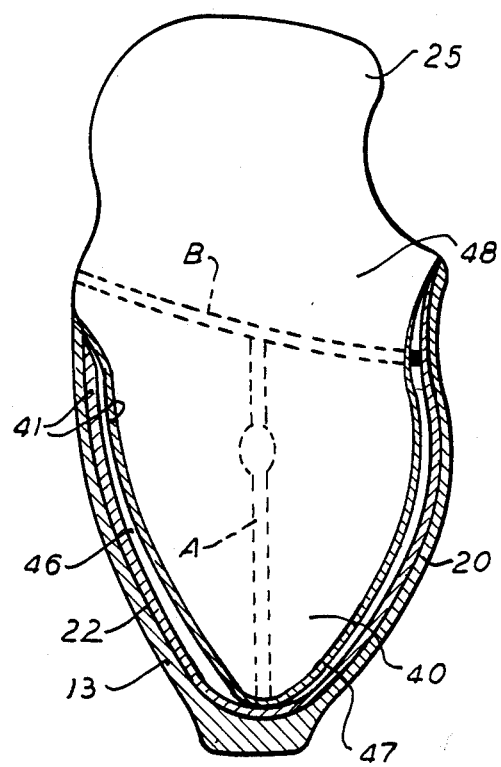
FIG. 8 shows a sectional view taken on the line 8—8 in FIG. 7 looking in the direction of the arrows.
Figure 7:
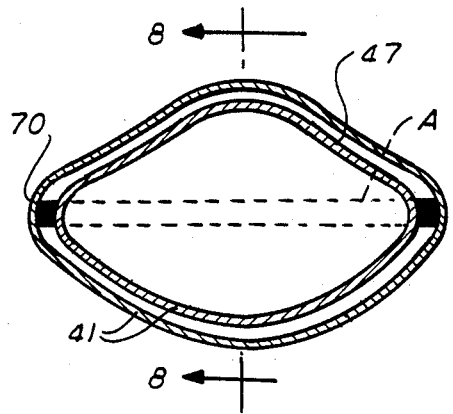
FIG. 7 shows a sectional view taken on the line 7—7 of FIG. 5 looking in the direction of the arrows.
Figure 5:
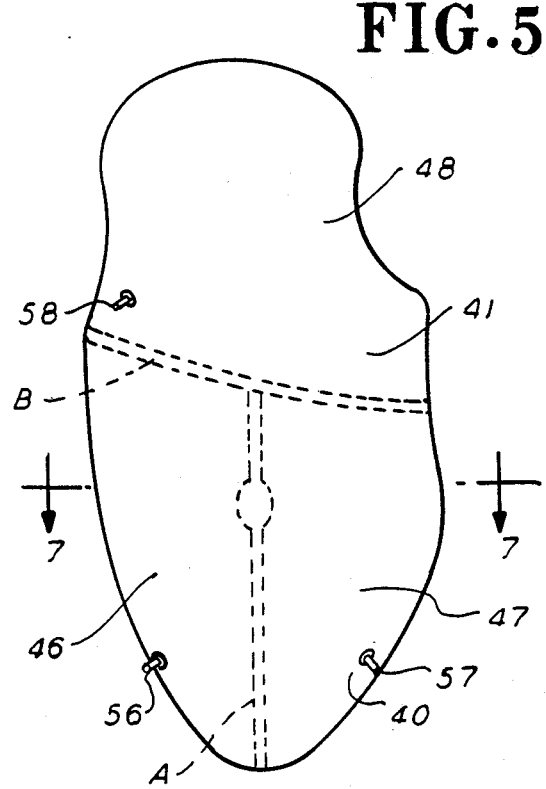
FIG. 5 shows a side elevation view of a portion of the device shown in FIG. 1.

The sock 40 is formed as a flexible, double-walled continuous membrane 41 that may be molded from a soft material such as polyurethane or the like. The molded shape of the inside surface of sock 40 should preferably be the same as the shape of the outer surface of the users limb when it is under static pressure of a nature that will generally be experienced by the user. The double-walled membrane 41 is bonded to itself along bonding surfaces A and B to form three inflatable bladders 46, 47, 48. The membranes 41 are preferably spaced from each other when in an unstressed condition as shown generally in FIG. 8. As such, the sock 40 defines bladders more precisely defined as a posterior bladder 46, an anterior bladder 47 and a proximal medialateral bladder 48. Bladders 46, 47, 48 have independent inflation valves 56, 57, 58, respectively, extending therefrom. Corresponding openings 66, 67, 68 are formed in the shell 13 to accommodate the valves 56, 57, 58 respectively. Each of the bladders 46, 47, 48 is individually inflatable, with air or other fluid medium, by the wearer so that the pressures therein can be adjusted independently of the pressures in the other bladders.

It is conceived that two or more of the bladders 46, 47, 48 could have equal pressures. In such cases, it is not necessary to have independent valves 56, 57, 58 since inflation of two bladders with a single valve will automatically result in equal pressures. What is important, generally, is that for those bladders having a common inflation valve, the bladders should be independent of each other during use to reduce undamped motions.

The shape of the bonding surface A is selected for each individual user to provide two functions. First, the bonding surface A defines part of the perimeters of bladders 46, 47. The locations of bladders 46, 47 are chosen to provide maximum weight-bearing areas for the stump. Additionally, the bladders 46, 47 are located on opposed surfaces of the stump to individually adsorb rotational forces created as the stump rotates the leg 11 forwardly and rearwardly during normal walking. A second function of the bonding surface A is to provide non-force-inducing areas over selected sensitive portions of the stump.

In the preferred embodiment and for the example shown, the medial tibial flare 70 and the area of the fibula head 71 are shown as areas of substantial sensitivity that do not receive significant forces. As such, bonding surface A extends vertically and mediolaterally and continuously from a point just below the medial femoral condyle 75 over the medial tibial flare 70 around the terminus 76 of the stump up to and over the fibula head 71 to a point just below the lateral femoral condyle 78. It is noted that the bonding surface A is enlarged in those areas adjacent the medial tibial flare 70 and the area of the fibula head 71 to provide a non-force-inducing surface of the proper shape and size at these locations. The end points of bonding surface A connects with bonding surface B which extends from the upper edge of bladder 46 around the front just over the tibial tubercle 79.

As pointed out above, the proximal mediolateral bladder 48 primarily provides lateral stability and retains the prosthesis on stump. As such, the bladder 48 extends proximal to and over the femoral condyles 75, 78, passing over the mid-patella tendon area 29 located just above the tibial tubercle 79. The anterior bladder 47 and the posterior bladder 46 primarily provide static and dynamic weight and force bearing support to the stump. These bladders contact the stronger areas of the stump capable of withstanding significant pressures as is generally known by those skilled in this art. As such, the anterior bladder 47 extends laterally to medially, encompassing the muscle belly of the tibialis anterior, tibial crest, the medial angle of the tibia, and the muscle belly of the anterior portion of the soleus muscle. The posterior bladder 46 begins at the back proximal edge of the poplitealfossa extending distilly to encompass the muscle belly of the soleus and the gastrocnemius.

Obviously many modifications and variations of the present invention are possible in the light of the above teachings. For example, a single-walled membrane may be bonded to selected portions of the interior surface 22 of the shell 13 to from appropriate bladders rather than having a removable sock as disclosed. Additionally, the valves 56, 57, 58 are shown as located at three spaced points that extend to the exterior of the shell 13. Alternatively, the three valves 56, 57, 58 could readily be grouped in a small defined location adjacent to each other for ready access by the user. Still further, when the prosthesis is to be used as an artificial arm or a leg for an above-the-knee amputee or elsewhere, it may be desirable to have two or more independent force-bearing bladders to provide opposed force-bearing surfaces in a plurality of transverse directions. Still further, additional or alternative elements may be employed for holding the prosthesis on the stump. For example, a vacumm mechanism on the prosthesis may interface with the stump for holding purposes. In many cases, the posterior and anterior bladders 46, 47 will provide a natural suction with the stump that will sufficiently hold the prosthesis on the stump thereby eliminating the need for the bladder 48 or any other holding means. It is therefore to be understood that, within the scope of the appended claims, the invention may be practiced otherwise than as specifically described herein.

What is claimed is:
1. A prosthesis comprising:
 a socket having a stump-receiving opening and a cup-shaped interior, said socket including an outer shell and a sock disposed therein;
 said sock including a plurality of bladders;
 means for inflating said bladders; and wherein
 said bladders cooperate to define a stump engaging surface, said stump engaging surface of said bladders being molded to have a shape conforming to the outer surface of the user's stump when the stump is under static pressure.

2. The prosthesis of claim 1 wherein said bladders include an anterior bladder and a posterior bladder.

3. The prosthesis of claim 2 and further including a third bladder, said third bladder for substantially surrounding said stump.

4. The prosthesis of claim 3 wherein said bladders define air chambers and each air chamber is fluidly separated from the others.

5. A prosthesis for a below-the-knee amputee comprising:

a support means for providing a weight-bearing support for a stump;

means for providing lateral stability to the user's knee;

said support means including an inflatable sock; said inflatable sock including, when not inflated, an inner surface which defines a shape conforming to the outer surface of the user's stump when the stump is under static pressure.

6. The prosthesis of claim 5 wherein said support means include a plurality of bladders and said plurality of bladders includes an anterior bladder and a posterior bladder for engaging said stump below the knee.

* * * * *